(12) United States Patent
Xue et al.

(10) Patent No.: US 12,350,208 B2
(45) Date of Patent: Jul. 8, 2025

(54) MOVABLE MEDICAL BED SYSTEM AND MRI APPARATUS

(71) Applicant: Siemens Healthcare GmbH, Erlangen (DE)

(72) Inventors: Ting Qiang Xue, Shenzhen (CN); JianMin Wang, Shenzhen (CN); Zhi Bin Li, Shenzhen (CN); Jian Hong Liu, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 0 days.

(21) Appl. No.: 17/677,164

(22) Filed: Feb. 22, 2022

(65) Prior Publication Data
US 2022/0265496 A1  Aug. 25, 2022

(30) Foreign Application Priority Data
Feb. 22, 2021  (CN) .......................... 202120392207.3

(51) Int. Cl.
*A61G 7/018* (2006.01)
*A61G 7/05* (2006.01)
*A61G 12/00* (2006.01)

(52) U.S. Cl.
CPC .............. *A61G 7/018* (2013.01); *A61G 7/05* (2013.01); *A61G 12/007* (2013.01);
(Continued)

(58) Field of Classification Search
CPC ...... A61G 7/018; A61G 7/05; A61G 2203/70; A61G 2210/50; A61G 7/08; A61G 13/00; A61G 7/002; A61G 7/005; A61G 7/008; A61G 7/012; A61G 7/015; A61B 5/055; H02J 50/90; H02J 50/12; H02J 50/10; H02J 50/70; H02J 2310/20; H02J 2310/22; H02J 2310/23; H02J 50/80; H02J 50/40; H02J 50/402; H04B 5/0037; H04B 1/3888

See application file for complete search history.

(56) References Cited

U.S. PATENT DOCUMENTS

| 2004/0120130 A1* | 6/2004 | Hensley | H05K 9/0015 |
| | | | 361/818 |
| 2018/0143274 A1* | 5/2018 | Poole | G01R 33/3852 |

(Continued)

FOREIGN PATENT DOCUMENTS

| CN | 109259967 A | * | 1/2019 | |
| DE | 102016211178 A1 | * | 12/2017 | |
| WO | WO-2013000330 A1 | * | 1/2013 | ............... A61G 1/02 |

*Primary Examiner* — David R Hare
*Assistant Examiner* — Deborah Talitha Gedeon
(74) *Attorney, Agent, or Firm* — Banner & Witcoff Ltd.

(57) ABSTRACT

A movable medical bed system may include a bed body and a power supply apparatus. The power supply apparatus may include an electrical energy receiver and an electrical energy transmitter. The electrical energy receiver is arranged on the bed body. The electrical energy transmitter is configured to be connected to a power source. The bed body is able to move to a working position relative to the electrical energy transmitter. When the bed body is located at the working position, the electrical energy receiver can engage in electrical energy transmission with the electrical energy transmitter without plugging-in. The movable medical bed system helps to make the supply of power more convenient.

21 Claims, 11 Drawing Sheets

(52) U.S. Cl.
CPC ........ *A61G 12/008* (2013.01); *A61G 2203/70* (2013.01); *A61G 2210/50* (2013.01)

(56) References Cited

U.S. PATENT DOCUMENTS

| | | | |
|---|---|---|---|
| 2018/0329422 A1* | 11/2018 | Biber | A61B 6/0487 |
| 2019/0123587 A1* | 4/2019 | Titov | A61G 7/05 |
| 2019/0123598 A1* | 4/2019 | Patmore | A61G 7/05 |
| 2020/0298716 A1* | 9/2020 | Su | H02J 50/10 |

* cited by examiner

MOVABLE MEDICAL BED SYSTEM AND MRI APPARATUS

CROSS REFERENCE TO RELATED APPLICATIONS

This patent application claims priority to Chinese Patent Application No. 202120392207.3, filed Feb. 22, 2021, which is incorporated herein by reference in its entirety.

BACKGROUND

Field

The present disclosure relates to a movable medical bed system, in particular a movable medical bed system for an MRI apparatus, and an MRI apparatus comprising same.

Related Art

A movable medical bed can move a patient conveniently between multiple target positions, e.g. move the patient from an operating room to a magnetic resonance examination room. Electrical equipment is often provided on medical beds; this electrical equipment is for example used for driving movement of a bed board of the medical bed, receiving RF signals, etc. At present, when a movable medical bed reaches a target position, a worker needs to manually plug in a power source plug in order to supply power to the electrical equipment on the medical bed, and when the medical bed needs to leave the target position, the worker also needs to manually unplug the power source plug. Frequent plugging-in and unplugging operations cannot meet the requirement for convenience.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
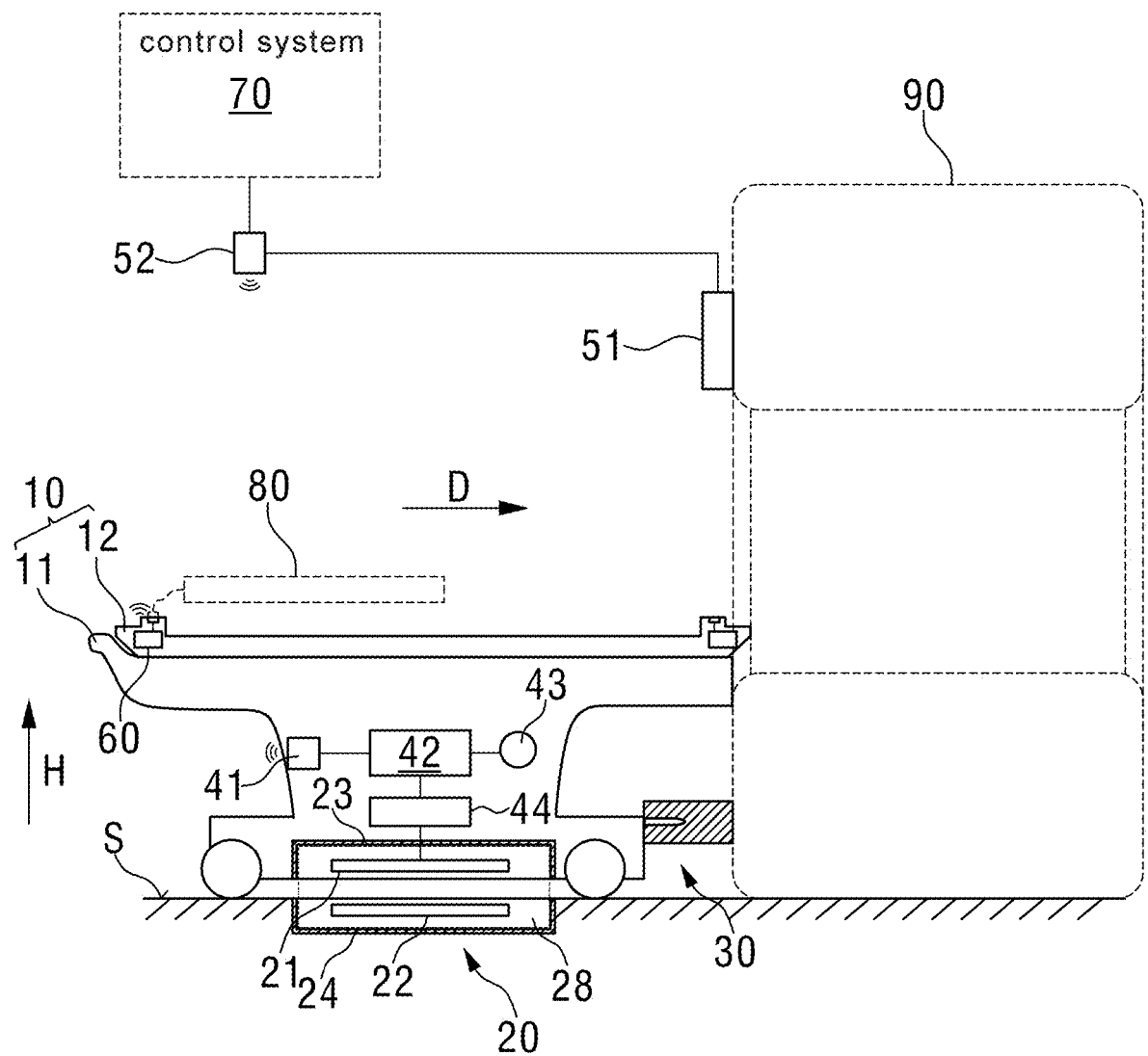
FIG. 1 is a structural schematic diagram of an exemplary embodiment of the movable medical bed system.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a movable medical bed system, which helps to make the supply of power more convenient.

Another object of the disclosure is to provide an MRI apparatus, wherein a movable medical bed system thereof helps to make the supply of power more convenient.

The present disclosure provides a movable medical bed system, comprising a bed body and a power supply apparatus. The power supply apparatus comprises a first element and a second element. The first element is arranged on the bed body. The second element is configured to be connected to a power source. The bed body is able to move to a working position relative to the second element. When the bed body is located at the working position, the first element is able to engage in electrical energy transmission with the second element without plugging-in.

In this movable medical bed system, when the bed body reaches the working position, the first element and second element can automatically engage in electrical energy transmission to achieve the supply of power, without the need for a worker to manually plug in a power source plug, thus helping to make the supply of power more convenient.

In another exemplary embodiment of the movable medical bed system, the first element is configured as a receiving coil, and the second element is configured as a transmitting coil, the receiving coil and the transmitting coil being able to engage in electrical energy transmission by inductive coupling. Electrical energy can thus be transmitted wirelessly. In addition, compared with a plug and socket, inductive coupling does not require high precision in the relative positions of the receiving coil and transmitting coil, thus allowing a certain degree of deviation when the bed body moves to the working position, and thus helping to improve the working efficiency.

In another exemplary embodiment of the movable medical bed system, the power supply apparatus further comprises a first shielding cover and a second shielding cover.

The first shielding cover is arranged on the bed body and able to shield an electromagnetic field. The second shielding cover is able to shield an electromagnetic field. The power supply apparatus is configured such that: when the bed body is located at the working position, the first shielding cover and the second shielding cover are able to enclose a shielding space, with the first element and the second element both being located in the shielding space. This can reduce the influence of electromagnetic interference generated by the receiving coil and transmitting coil on the surrounding environment.

In another exemplary embodiment of the movable medical bed system, the first element is arranged at the bottom of the bed body in a height direction of the bed body. The second element is configured such that: when the bed body is located at the working position, the second element is located at a side of the bed body that is close to the bottom in the height direction, and the second element is arranged opposite the first element in the height direction. This makes it possible to have a larger space to arrange a larger coil, thus helping to make the supply of power more efficient.

In another exemplary embodiment of the movable medical bed system, the bed body can move with a docking attitude (interface) to the working position in a docking direction. The first element is arranged at one end of the bed body in the docking direction in the docking attitude (interface). The second element is configured such that: when the bed body is located at the working position, the second element is located at a side of the bed body that is close to the first element in the docking direction, and the second element is arranged opposite the first element in the docking direction. This structure is simple, and facilitates manufacture.

In another exemplary embodiment of the movable medical bed system, the bed body can move to the working position in a docking direction. One of the first element and the second element is configured as an electrically conductive body, while the other is configured as an electrically conductive rail extending in the docking direction. When the bed body is located at the working position, the electrically conductive body and the electrically conductive rail can engage in electrical energy transmission through contact. Compared with a plug and socket, high precision is not required in the relative positions of the electrically conductive body and electrically conductive rail, thus allowing a certain degree of deviation when the bed body moves to the working position, and thus helping to improve the working efficiency.

In another exemplary embodiment of the movable medical bed system, the bed body can move to the working position in a docking direction. The movable medical bed system further comprises a docking guidance apparatus. The docking guidance apparatus comprises an insertion member and a guiding member. One of the insertion member and the guiding member is fixed to the bed body. The guiding member has a plug-in slot. As the bed body moves to the working position in the docking direction, the insertion member is inserted into the plug-in slot of the guiding member. When the bed body is located at the working position, a slot wall of the plug-in slot is able, through abutment with the insertion member, to restrict shifting of the bed body in a direction perpendicular to the docking direction. The docking guidance apparatus helps to guide the bed body to move to the working position accurately, and keeps the bed body stable in the working position.

In another exemplary embodiment of the movable medical bed system, a free end of the insertion member is configured to have a pointed shape, gradually contracting toward the center in the docking direction. The bottom of the plug-in slot in the docking direction has the same shape as the free end of the insertion member. This can increase the success rate of insertion of the insertion member into the guiding member, thus helping to improve the working efficiency.

In another exemplary embodiment of the movable medical bed system, the movable medical bed system further comprises a first wireless communication module, a drive controller and an electric motor. The first wireless communication module is arranged on the bed body. The first wireless communication module is able to receive a drive control signal by wireless telecommunication or optical wireless communication. The drive controller is arranged on the bed body and connected to the first wireless communication module in order to receive the drive control signal. The drive controller is able to acquire electrical energy via the first element. The electric motor is arranged on the bed body and connected to the drive controller. The drive controller is able to control the running of the electric motor according to the drive control signal. The electric motor can thus be controlled wirelessly.

In another exemplary embodiment of the movable medical bed system, the movable medical bed system further comprises a battery. The drive controller is connected to the battery in order to acquire electrical energy. The first element is connected to the battery in order to charge the battery. The battery can supply power to the drive controller when the first element and second element have not yet engaged in electrical energy transmission.

In another exemplary embodiment of the movable medical bed system, the movable medical bed system further comprises an operating panel and a second wireless communication module. The operating panel is used to generate the drive control signal according to an operation performed thereon by a user. The second wireless communication module is connected to the operating panel. The operating panel is able to send the drive control signal to the first wireless communication module via the second wireless communication module by wireless telecommunication or optical wireless communication. The operating panel enables the electric motor to be controlled more conveniently.

In another exemplary embodiment of the movable medical bed system, the bed body comprises a bed frame and a bed board. The bed board is movably connected to the bed frame. The electric motor is able to drive the bed board to move relative to the bed frame. This makes it easy to move patients.

In another exemplary embodiment of the movable medical bed system, the movable medical bed system further comprises a communication module. The communication module is arranged on the bed body and comprises an analog-to-digital converter, a digital signal processor and a third wireless communication module. The analog-to-digital converter is configured to be connected to an RF coil. The digital signal processor is connected to the analog-to-digital converter. The third wireless communication module is connected to the digital signal processor and configured to communicate with a control system by wireless telecommunication or optical wireless communication. Wireless communication between the RF coil and the control system can thus be achieved.

The present disclosure also provides an MRI apparatus, comprising a movable medical bed system as described above. When the bed body of the MRI apparatus reaches the working position, the first element and second element can automatically engage in electrical energy transmission to achieve the supply of power, without the need for a worker to manually plug in a power source plug, thus helping to make the supply of power more convenient.

In another exemplary embodiment of the MRI apparatus, the MRI apparatus further comprises a control system and a second wireless communication module. The control system is able to generate a drive control signal. The second wireless communication module is connected to the control system. The control system is able to send the drive control signal to the first wireless communication module via the second wireless communication module by wireless telecommunication or optical wireless communication. The electric motor can thus be controlled wirelessly.

In another exemplary embodiment of the MRI apparatus, the MRI apparatus further comprises an RF coil, a control system and a second wireless communication module. The RF coil is connected to the analog-to-digital converter. The second wireless communication module is connected to the control system and able to communicate with the third wireless communication module by wireless telecommunication or optical wireless communication. Wireless communication between the RF coil and the control system can thus be achieved.

FIG. 1 is a structural schematic diagram of an exemplary embodiment of the movable medical bed system. As shown in FIG. 1, the movable medical bed system comprises a bed body 10 and a power supply apparatus 20.

The bed body 10 is used to carry a patient. In this exemplary embodiment, the bed body 10 for example comprises a bed frame 11 and a bed board 12. The bed board 12 is arranged on the bed frame 11, and the bed frame 11 is for example able move on a floor S by means of rollers.

The power supply apparatus 20 comprises a first element 21 and a second element 22. The first element 21 is arranged on the bed body 10, and is connected to electrical equipment on the bed body 10. The second element 22 is configured to be connected to a power source. The bed body 10 can move to a working position relative to the second element 22 (the bed body 10 shown in FIG. 1 is located at the working position). When the bed body 10 is located at the working position, the first element 21 can engage in electrical energy transmission with the second element 22 without plugging-in. Specifically, in this exemplary embodiment, the first element 21 is configured as a receiving coil, and the second element 22 is configured as a transmitting coil; when the bed body 10 is located at the working position, the receiving coil and transmitting coil can engage in electrical energy transmission by inductive coupling. Thus, when the bed body 10 reaches the working position, the first element 21 and second element 22 can automatically engage in electrical energy transmission to achieve the supply of power, without the need for a worker to manually plug in a power source plug, thus helping to make the supply of power more convenient.

In addition, compared with a plug and socket, inductive coupling does not require high precision in the relative positions of the receiving coil and transmitting coil, thus allowing a certain degree of deviation when the bed body 10 moves to the working position, and thus helping to improve the working efficiency.

In this exemplary embodiment, the first element 21 is arranged at the bottom of the bed body 10 in a height direction H of the bed body 10. The second element 22 is configured such that: when the bed body 10 is located at the working position, the second element 22 is located at a side of the bed body 10 that is close to the bottom in the height direction H, and the second element 22 is arranged opposite the first element 21 in the height direction H. The second element 22 may for example be mounted at a lower side of the floor S, in order to prevent knocks or prevent the movement of the bed body 10 from being affected. Having the first element 21 arranged at the bottom of the bed body 10 makes it possible to have a larger space to arrange a larger coil, thus helping to make the supply of power more efficient.

Figure 2:
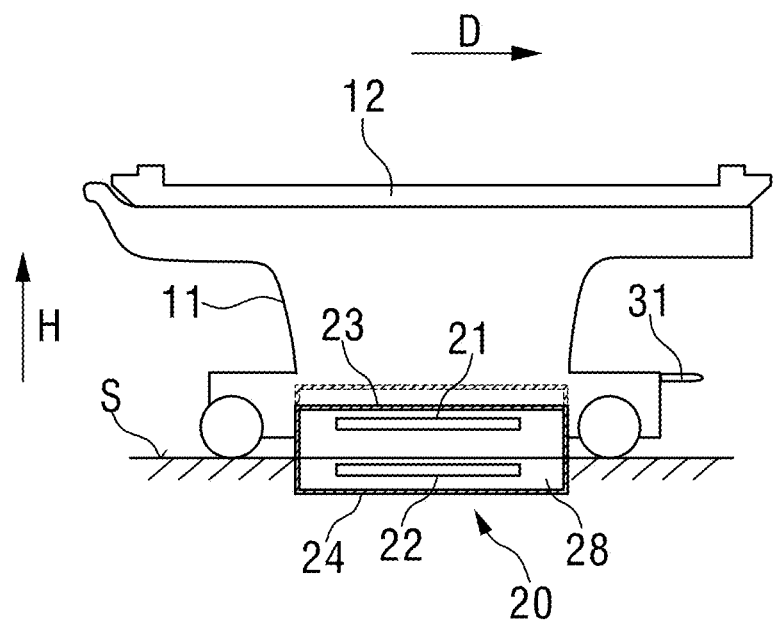
FIG. 2 illustrates an exemplary embodiment of the first shielding cover and second shielding cover.

As shown in FIG. 1, in this exemplary embodiment, the power supply apparatus 20 further comprises a first shielding cover 23 and a second shielding cover 24. The first shielding cover 23 is arranged on the bed body 10 and is able to shield an electromagnetic field. The second shielding cover 24 is able to shield an electromagnetic field. The power supply apparatus 20 is configured such that: when the bed body 10 is located at the working position, the first shielding cover 23 and second shielding cover 24 are able to enclose a shielding space 28, with the first element 21 and second element 22 both being located in the shielding space 28. This can reduce the influence of electromagnetic interference generated by the receiving coil and transmitting coil on the surrounding environment. In this exemplary embodiment, the first shielding cover 23 is fixed to the bed body 10, and the second shielding cover 24 is fixed below the floor; in order to ensure that the bed body 10 can move unobstructed, a gap is often left between the first shielding cover 23 and the second shielding cover 24, but such a configuration affects the shielding result. To solve this problem, in other exemplary embodiments, the following configuration is possible: when the bed body 10 is located at the working position, the first shielding cover 23 and second shielding cover 24 can move relative to each other to eliminate or reduce the gap; for example, as shown in the FIG. 2, the first shielding cover 23 can move to the solid-line position from the dotted-line position, thereby improving the shielding result.

Figure 3:
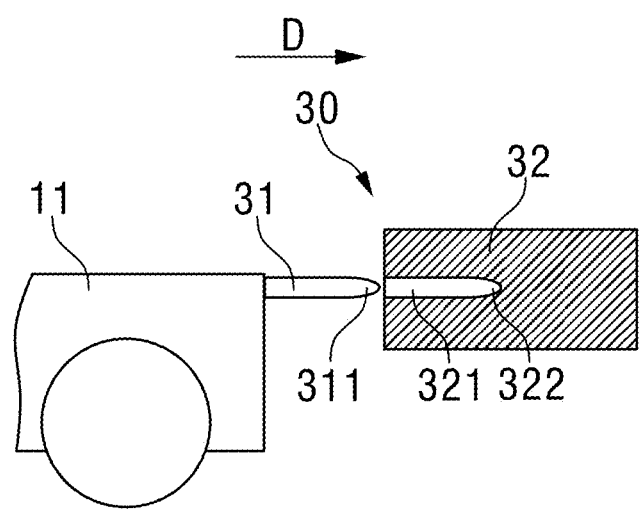
FIG. 3 is a structural schematic diagram showing a docking guidance apparatus according to an exemplary embodiment.

As shown in FIG. 1, in this exemplary embodiment, the bed body 10 can move with a docking attitude (interface) to the working position in a docking direction D. The movable medical bed system further comprises a docking guidance apparatus 30. As shown in FIG. 3, the docking guidance apparatus 30 comprises an insertion member 31 and a guiding member 32. The insertion member 31 is fixed to the bed frame 11. The guiding member 32 is arranged in a fixed manner relative to the floor, e.g. may be fixed to a magnet system 90 of an MRI apparatus. The guiding member 32 has a plug-in slot 321. As the bed body 10 moves to the working position in the docking direction D, the insertion member 31 is inserted into the plug-in slot 321 of the guiding member 32. As shown in FIG. 1, when the bed body 10 is located at the working position, a slot wall of the plug-in slot 321 is able, through abutment with the insertion member 31, to restrict shifting of the bed body 10 in a direction perpendicular to the docking direction D. The docking guidance apparatus 30 helps to guide the bed body 10 to move to the working position accurately, and keeps the bed body 10 stable in the working position.

As shown in FIG. 3, in this exemplary embodiment, a free end 311 of the insertion member 31 is configured to have a pointed shape, gradually contracting toward the center in the docking direction D. The bottom 322 of the plug-in slot 321 in the docking direction D has the same shape as the free end 311 of the insertion member 31. This can increase the success rate of insertion of the insertion member 31 into the guiding member 32, thus helping to improve the working efficiency.

As shown in FIG. 1, in this exemplary embodiment, the movable medical bed system further comprises a first wireless communication module (first wireless transceiver) 41, a drive controller 42 and an electric motor 43. The first wireless communication module 41 is arranged on the bed body 10. The first wireless communication module 41 can receive a drive control signal by wireless telecommunication. The drive controller 42 is arranged on the bed body 10, and connected to the first wireless communication module 41 in order to receive the drive control signal. The electric motor 43 is arranged on the bed body 10 and connected to the drive controller 42. The drive controller 42 can control the running of the electric motor 43 according to the drive control signal. In this exemplary embodiment, the bed board 12 is movably connected to the bed frame 11, and the electric motor 43 can drive the bed board 12 to move relative to the bed frame 11. In an exemplary embodiment, the controller 42 includes processing circuitry that is configured to perform one or more functions and/or operations of the controller 42.

The drive controller 42 can acquire electrical energy via the first element 21. In this exemplary embodiment, the movable medical bed system further comprises a battery 44. The drive controller 42 is connected to the battery 44 in order to obtain electrical energy. The first element 21 is connected to the battery 44 in order to charge the battery 44. The battery 44 can supply power to the drive controller 42 when the first element 21 and second element 22 have not yet engaged in electrical energy transmission. However, there is no restriction to this. In an exemplary embodiments, the battery 44 need not be provided, and the drive controller 42 may be connected to the first element 21 via an energy regulating module, which can convert AC electricity from the first element 21 to DC electricity, and then supply this to the drive controller 42. In other exemplary embodiments, the number of electric motor(s) 43 may be adjusted as needed, and the object of the driving action of the electric motor 43 may also be adjusted as needed; for example, it may also be used to drive movement of the bed body 10 on the floor S.

As shown in FIG. 1, in this exemplary embodiment, the movable medical bed system further comprises an operating panel 51 and a second wireless communication module (second wireless transceiver) 52. The operating panel 51 is for example a touch control panel or a push-key panel, and is for example mounted on the magnet system 90 of the MRI apparatus. The operating panel 51 is used to generate a drive control signal according to an operation performed thereon by a user. The second wireless communication module 52 is connected to the operating panel 51. The operating panel 51 can send the drive control signal to the first wireless communication module 41 via the second wireless communication module 52 by wireless telecommunication. The operating panel 51 enables the electric motor 43 to be controlled more conveniently.

Figure 4:
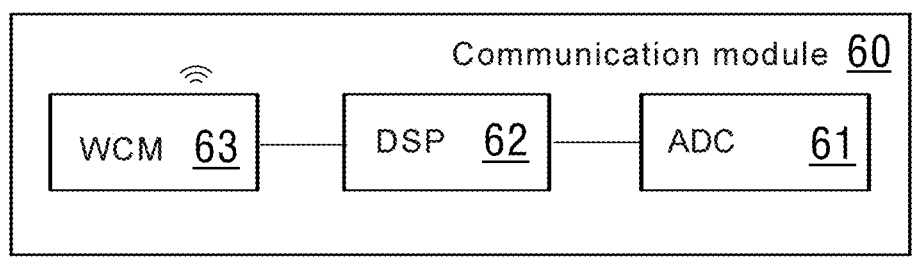
FIG. 4 is a structural block diagram of the communication module according to an exemplary embodiment.

As shown in FIG. 1, in this exemplary embodiment, the movable medical bed system further comprises a communication module (transceiver) 60. The communication module 60 is arranged on the bed body 10; specifically, it is arranged on the bed board 12 for example. FIG. 4 is a block diagram of the structure of the communication module; as shown in FIG. 4, the communication module 60 comprises an analog-to-digital converter 61, a digital signal processor 62 and a third wireless communication module (third wireless transceiver) 63. Referring to both FIG. 1 and FIG. 4, the analog-to-digital converter 61 is configured to be connected to an RF coil 80 of the MRI apparatus. The digital signal processor 62 is connected to the analog-to-digital converter 61. The third wireless communication module 63 is connected to the digital signal processor 62, and configured to communicate with a control system 70 by wireless telecommunication. The control system 70 is for example a control system of the MRI apparatus. By means of the communication module 60, an RF signal of the RF coil 80 can be transmitted to the control system 70, and a control signal of the control system 70 can be transmitted to the RF coil 80, thereby achieving wireless communication between the RF coil 80 and the control system 70. As would be appreciated by one of ordinary skill in the art, one or more of the transceivers may be configured as a transmitter, a receiver, or a combination that includes both a transmitter and receiver.

Figure 5:
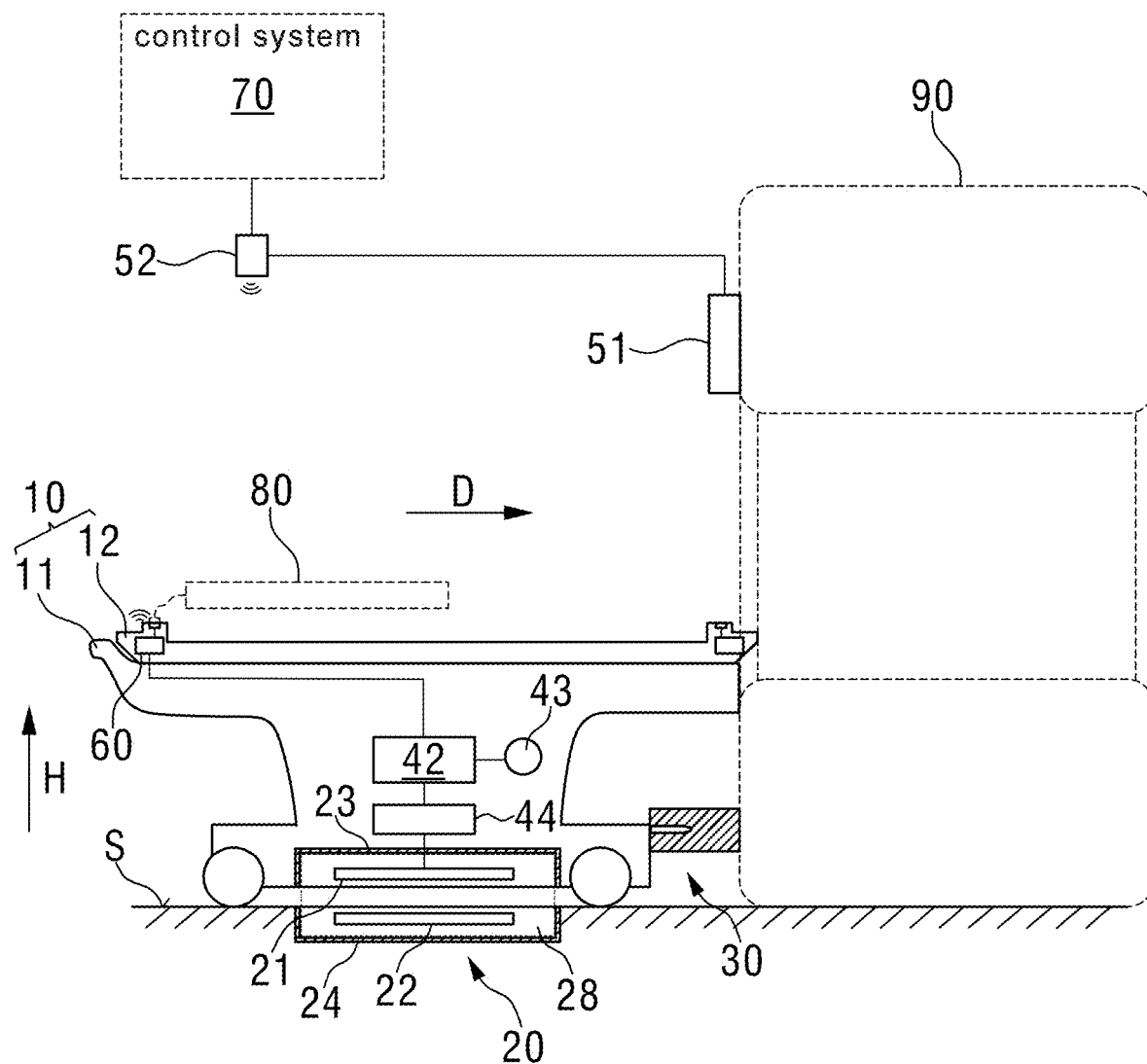
FIG. 5 is a structural schematic diagram of another exemplary embodiment of the movable medical bed system.
Figure 6:
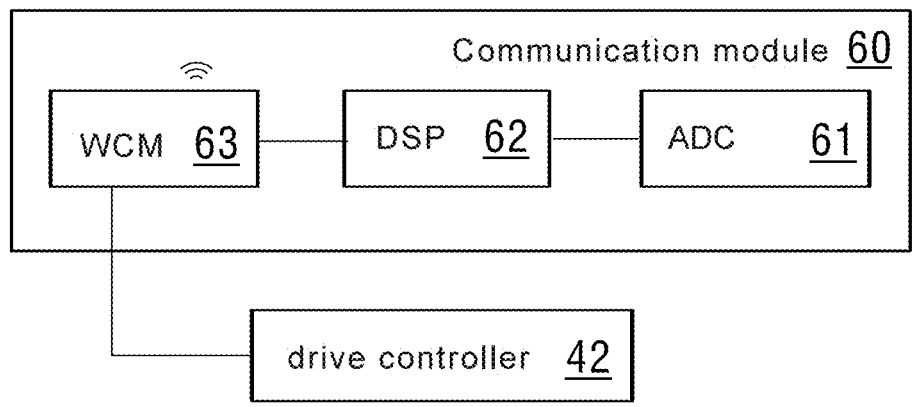
FIG. 6 illustrates the connection relationship between the drive controller and the communication module in the movable medical bed system shown in FIG. 5, according to an exemplary embodiment.

FIG. 5 is a structural schematic diagram of another exemplary embodiment of the movable medical bed system. Features of the movable medical bed system in this exemplary embodiment which are identical or similar to those of the movable medical bed system shown in FIG. 1 are not described again here. Unlike the latter, in this exemplary embodiment, the first wireless communication module 41 is not provided; instead, the drive controller 42 is connected to the third wireless communication module 63 of the communication module 60. FIG. 6 shows the connection relationship between the drive controller 42 and the communication module 60 in the movable medical bed system shown in FIG. 5; on this basis, the drive controller 42 can receive a drive control signal via the third wireless communication module 63 by wireless telecommunication. This enables costs to be reduced.

In an exemplary embodiment, it is also possible to replace the third wireless communication module 63 with a first photoelectric converter, and replace the second wireless communication module 52 with a second photoelectric converter. The first photoelectric converter is connected by optical fibre to a first optical cable connector arranged on the bed body 10. As the bed body 10 moves to the working position in the docking direction D, the first optical cable connector can dock with a second optical cable connector. The second optical cable connector is connected by optical fibre to the second photoelectric converter.

Figure 7:
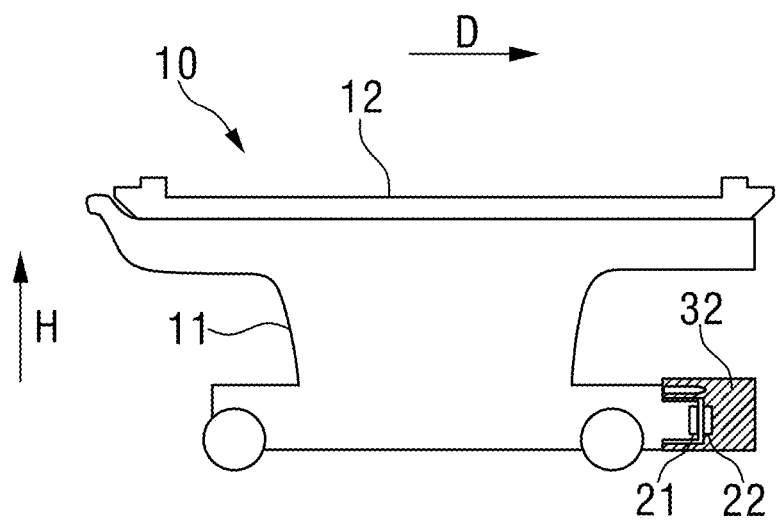
FIG. 7 is a structural schematic diagram that illustrates an arrangement of the first element and second element according to an exemplary embodiment.
Figure 8:
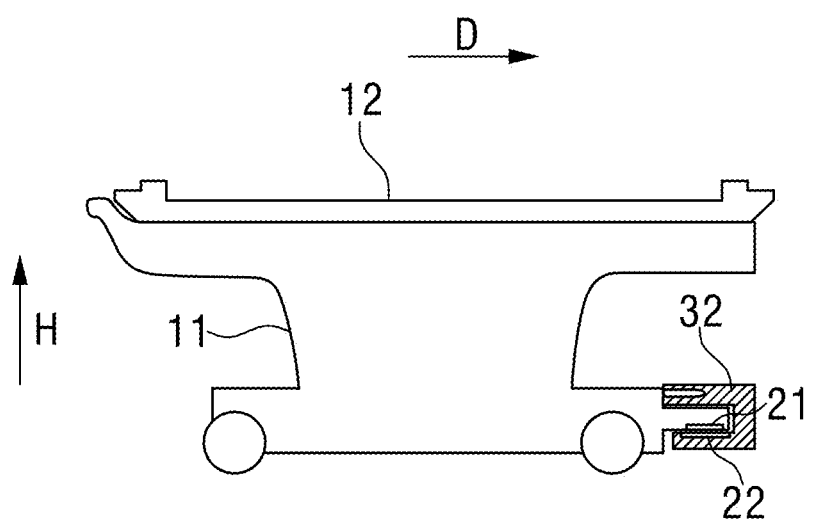
FIG. 8 is a structural schematic diagram that illustrates an arrangement of the first element and second element according to an exemplary embodiment.

In the movable medical bed systems shown in FIGS. 1 and 5, the first element 21 is arranged at the bottom of the bed body 10, in the height direction H of the bed body 10. However, there is no restriction to this. FIG. 7 shows another arrangement of the first element 21 and second element 22. As shown in FIG. 7, the first element 21 may also be arranged at one end of the bed body 10 in the docking direction D in the docking attitude (interface); and the second element 22 is configured such that: when the bed body 10 is located at the working position (the bed body 10 shown in FIG. 7 is located at the working position), the second element 22 is located at a side of the bed body 10 that is close to the first element 21 in the docking direction D, and the second element 22 is arranged opposite the first element 21 in the docking direction D. The second element 22 is for example arranged on the guiding member 32. FIG. 8 shows another arrangement of the first element 21 and second element 22. As shown in FIG. 8, the first element 21 may also be arranged at one end of the bed body 10 in the docking direction D in the docking attitude (interface); and the second element 22 is configured such that: when the bed body 10 is located at the working position (the bed body 10 shown in FIG. 8 is located at the working position), the second element 22 is arranged opposite the first element 21 in the height direction H of the bed body 10.

Figure 9:
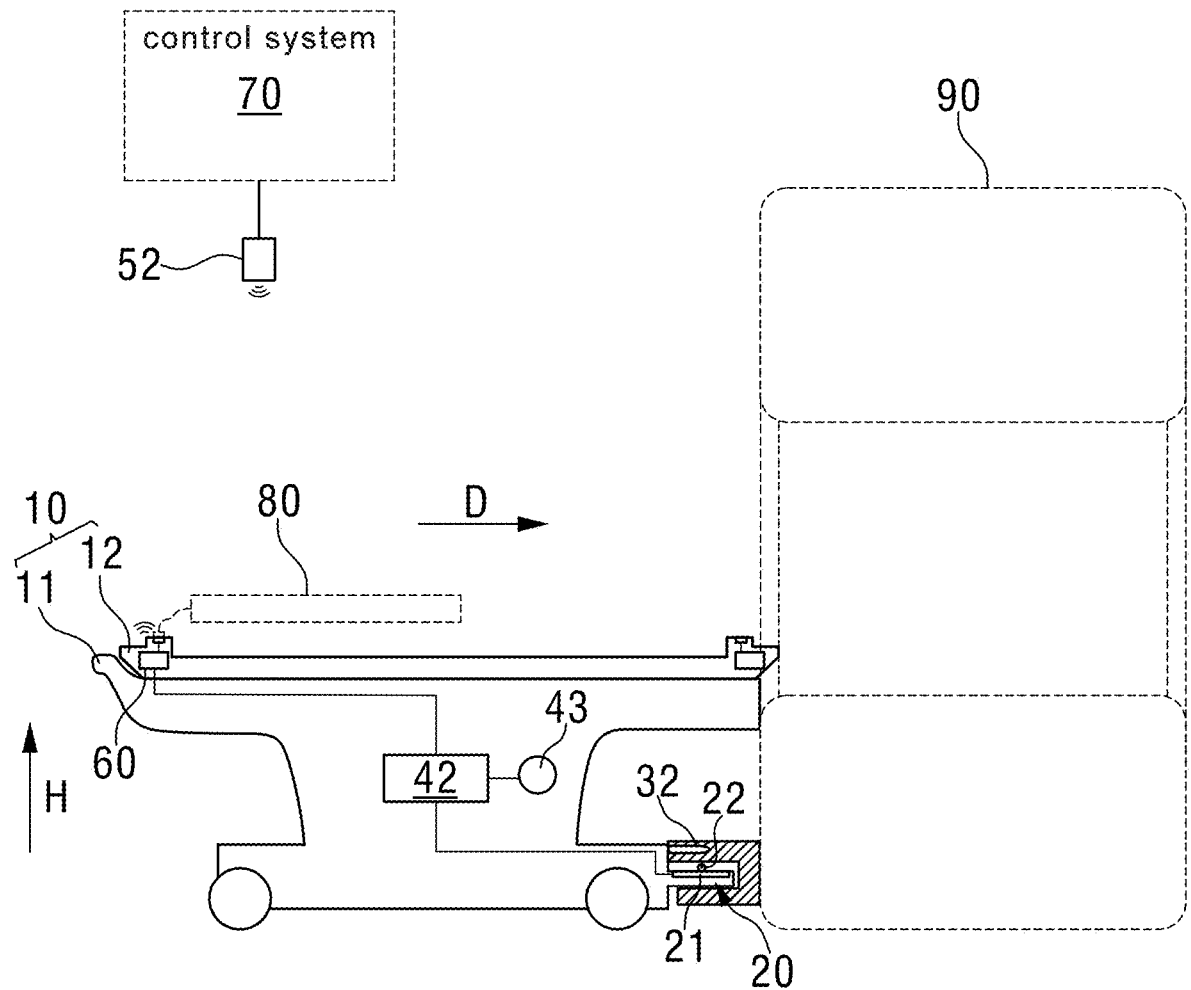
FIG. 9 is a structural schematic diagram of an exemplary embodiment of the movable medical bed system.

FIG. 9 is a structural schematic diagram of another exemplary embodiment of the movable medical bed system. Features of the movable medical bed system in this exemplary embodiment which are identical or similar to those of the movable medical bed system shown in FIG. 5 are not described again here; features which differ are as follows. In this exemplary embodiment, the first element 21 is configured as an electrically conductive rail, while the second element 22 is configured as an electrically conductive body; the electrically conductive rail extends in the docking direction D, and the electrically conductive body is for example an electrically conductive brush or electrically conductive wheel. When the bed body 10 is located at the working position, the electrically conductive body and electrically conductive rail can engage in electrical energy transmission through contact. Thus, when the bed body 10 reaches the working position, the first element 21 and second element 22 can automatically engage in electrical energy transmission to achieve the supply of power, without the need for a worker to manually plug in a power source plug, thus helping to make the supply of power more convenient.

In addition, compared with a plug and socket, high precision is not required in the relative positions of the electrically conductive body and electrically conductive rail, thus allowing a certain degree of deviation when the bed body 10 moves to the working position, and thus helping to improve the working efficiency.

In this exemplary embodiment, no operating panel 51 is provided; drive control signals may for example be generated by the control system 70 of the MRI apparatus and sent to the third wireless communication module 63 of the communication module 60 via the second wireless communication module 52 by wireless telecommunication, and transmitted to the drive controller 42 by the third wireless communication module 63. The equipment can thus be simplified.

In this exemplary embodiment, no battery 44 is provided, and the drive controller 42 is directly connected to the first element 21, thus simplifying the structure.

Figure 10:
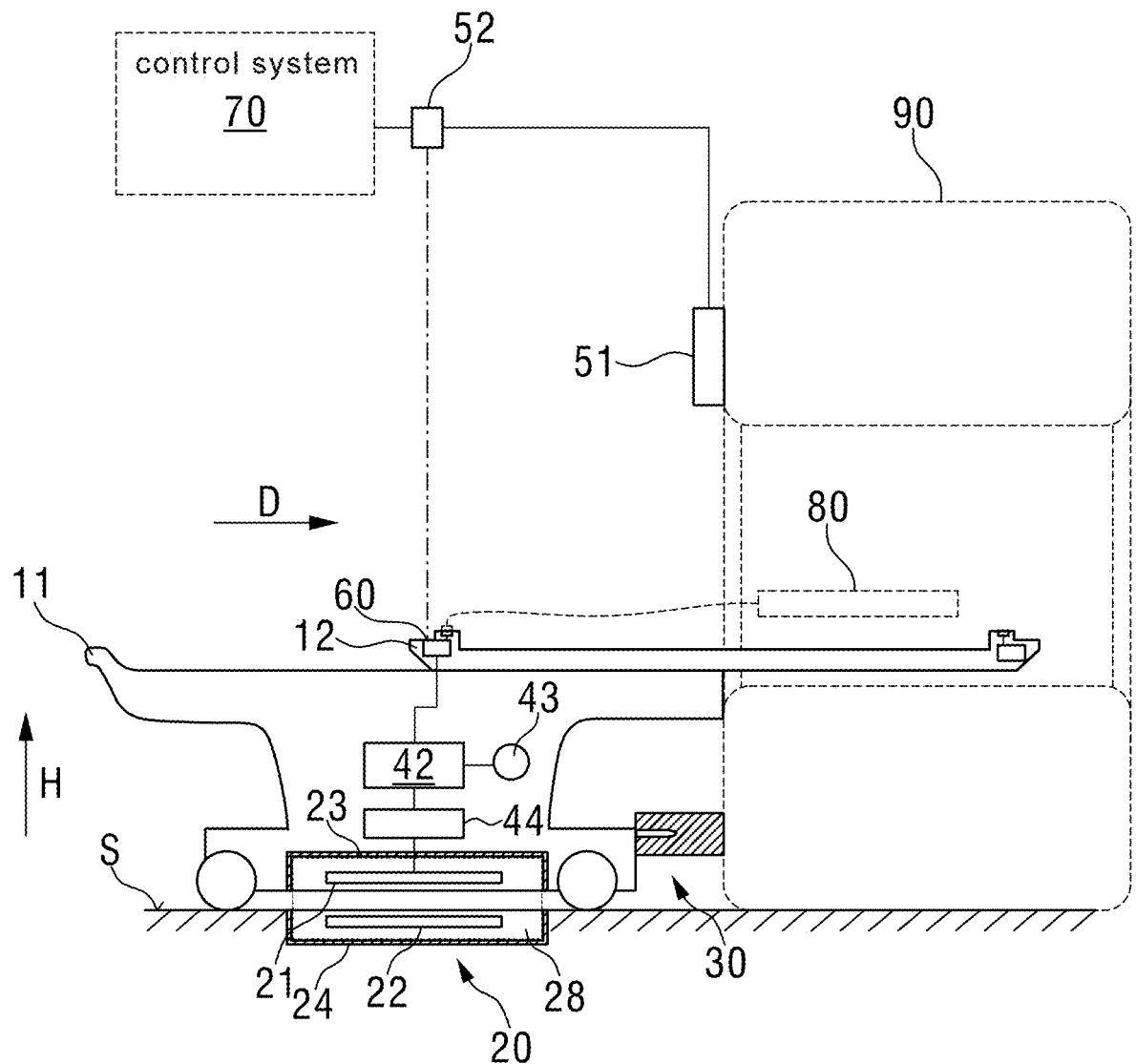
FIG. 10 is a structural schematic diagram of an exemplary embodiment of the movable medical bed system.

FIG. 10 is a structural schematic diagram of another exemplary embodiment of the movable medical bed system. Features of the movable medical bed system in this exemplary embodiment which are identical or similar to those of the movable medical bed system shown in FIG. 5 are not described again here; features which differ are as follows. In this exemplary embodiment, the second wireless communication module 52 engages in information transmission with the third wireless communication module 63 by optical wireless communication. The second wireless communication module 52 is for example arranged on a roof, while the third wireless communication module 63 is for example arranged at one end of the bed board 12, in order to meet the requirement for linear transmission in optical wireless communication. Optical wireless communication has the advantage that the available bandwidth is wider.

Figure 11:
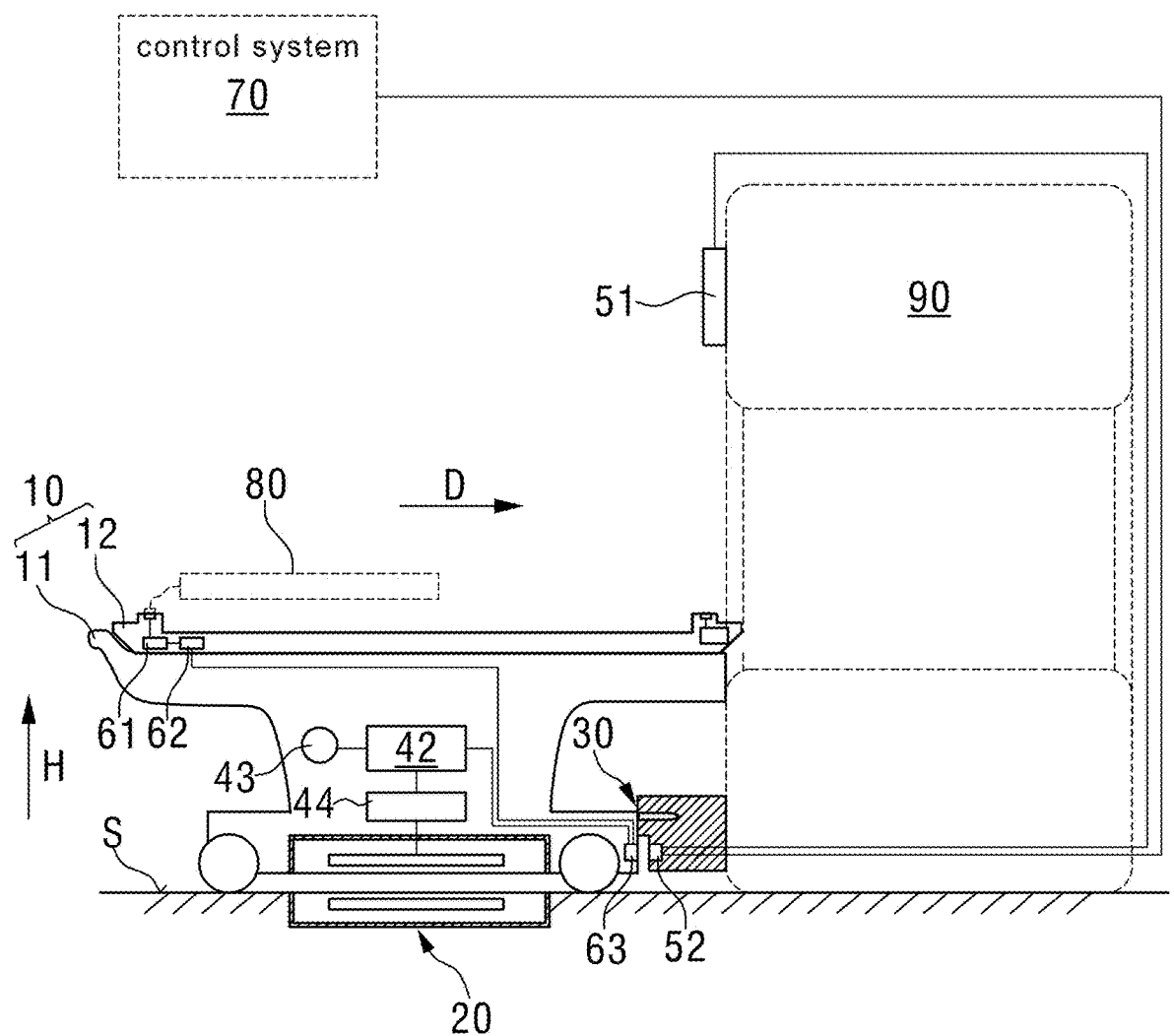
FIG. 11 is a structural schematic diagram of an exemplary embodiment of the movable medical bed system.

FIG. 11 is a structural schematic diagram of another exemplary embodiment of the movable medical bed system. Features of the movable medical bed system in this exemplary embodiment which are identical or similar to those of the movable medical bed system shown in FIG. 10 are not described again here. Unlike the latter, the second wireless communication module 52 is arranged on the guiding member 32, while the third wireless communication module 63 is arranged on a part of the bed body 10 where the insertion member 31 is arranged. This helps to reduce the distance between the second wireless communication module 52 and the third wireless communication module 63, in order to reduce the influence of the environment on signal transmission.

The present disclosure also provides an MRI apparatus which, in an exemplary embodiment thereof, comprises any one of the movable medical bed systems described above. Thus, when the bed body 10 of the MRI apparatus reaches the working position, the first element 21 and second element 22 can automatically engage in electrical energy transmission to achieve the supply of power, without the need for a worker to manually plug in a power source plug, thus helping to make the supply of power more convenient.

In an exemplary embodiment, the MRI apparatus further comprises a control system 70, an RF coil 80 and a magnet system 90. The magnet system 90 is configured to generate the magnetic field needed for imaging by the MRI apparatus. The control system 70 can generate a drive control signal. The second wireless communication module 52 is connected to the control system 70. The control system 70 can send the drive control signal to the drive controller 42 via the first wireless communication module 41 or the third wireless communication module 63 by wireless telecommunication or optical wireless communication via the second wireless communication module 52. Thus, by operating the control system 70, the drive control signal can be outputted in order to control the electric motor 43. The RF coil 80 is connected to the analog-to-digital converter 61; in an exemplary embodiment, the RF coil 80 is connected to the analog-to-digital converter 61 by means of a plug/socket assembly in such a way as to be pluggable/unpluggable. The second wireless communication module 52 can communicate with the third wireless communication module 63 by wireless telecommunication or optical wireless communication. By means of the communication module 60, an RF signal of the RF coil 80 can be transmitted to the control system 70, and a control signal of the control system 70 can be transmitted to the RF coil 80, thereby achieving wireless communication between the RF coil 80 and the control system 70. In an exemplary embodiment, one or more of the communication modules 41, 52, 60, and 63 includes processing circuitry that is configured to perform one or more functions of the communication module(s), including performing wireless and/or optical communications.

In each of the exemplary embodiments described above, wireless telecommunication can be replaced with optical wireless communication.

It should be understood that although the description herein is based on various embodiments, it is by no means the case that each embodiment contains just one independent technical solution. Such a method of presentation is adopted herein purely for the sake of clarity. Those skilled in the art should consider the description in its entirety. The technical solutions in the various embodiments could also be suitably combined to form other embodiments capable of being understood by those skilled in the art.

The series of detailed explanations set out above are merely particular explanations of feasible embodiments of the present disclosure, which are not intended to limit the scope of protection thereof. All equivalent embodiments or changes made without departing from the artistic spirit of the present disclosure, such as feature combinations, separations or repetitions, shall be included in the scope of protection thereof.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST 10 bed body
11 bed frame
12 bed board
20 power supply apparatus
21 first element (electrical energy receiver)
22 second element (electrical energy transmitter)
23 first shielding cover
24 second shielding cover
28 shielding space
30 docking guidance apparatus
31 insertion member
311 free end
32 guiding member
321 plug-in slot
322 bottom of plug-in slot
41 first wireless communication module
42 drive controller
43 electric motor
44 battery
51 operating panel
52 second wireless communication module
60 communication module
61 analog-to-digital converter
62 digital signal processor
63 third wireless communication module
70 control system
80 RF coil
90 magnet system
H height direction of bed body
D docking direction
S floor

The invention claimed is:

1. A movable medical bed system, comprising: a bed body including a bed frame, a bottom of the bed frame being spaced above a ground surface in a first direction; and
a power supply apparatus, including: an electrical energy receiver disposed at the bottom of the bed frame;
an electrical energy transmitter disposed on or below the ground surface and configured to be connected to a power source, the bed body being moveable to a working position relative to the electrical energy transmitter in a second direction perpendicular to the first direction, wherein, in response to the bed body being located at the working position, the electrical energy receiver being spaced from the electrical energy transmitter in the first direction and configured to engage in electrical energy transmission, in the first direction, with the electrical energy transmitter without plugging-in;

a first shielding cover arranged on the bed frame and being configured to shield an electromagnetic field; and a second shielding cover configured to shield an electromagnetic field, wherein, in response to the bed body being located at the working position, the first shielding cover and the second shielding cover are arranged opposite one another in the first direction, and the first shielding cover is configured to move away from the bottom of the bed frame towards the second shielding cover to reduce a distance between the first shielding cover and the second shield cover in the first direction and collectively define a shielding space, the electrical energy receiver and the electrical energy transmitter being located in the shielding space.

2. The movable medical bed system as claimed in claim 1, wherein the electrical energy receiver is configured as a receiving coil, and the electrical energy transmitter is configured as a transmitting coil, the receiving coil and the transmitting coil being configured to engage in electrical energy transmission by inductive coupling.

3. The movable medical bed system as claimed in claim 2, wherein:
the electrical energy transmitter is configured such that: in response to the bed body being located at the working position, the electrical energy transmitter is located at a side of the bed body closer to the bottom in the first direction, and the electrical energy transmitter is arranged opposite the electrical energy receiver in the first direction.

4. The movable medical bed system as claimed in claim 2, wherein:
the bed body is moveable with a docking interface to the working position in a docking direction that corresponds to the second direction;
the electrical energy receiver is arranged, at one end of the bed body in the docking direction, in the docking interface; and
the electrical energy transmitter is configured such that: in response to the bed body being located at the working position, the electrical energy transmitter is located at a side of the bed body that is closer to the electrical energy receiver in the docking direction, and the electrical energy transmitter is arranged opposite the electrical energy receiver in the docking direction.

5. The movable medical bed system as claimed in claim 1, wherein:
the bed body is moveable to the working position in a docking direction that corresponds to the second direction;
one of the electrical energy receiver and the electrical energy transmitter is configured as an electrically conductive body, while another of the electrical energy receiver and the electrical energy transmitter is configured as an electrically conductive rail extending in the docking direction; and
in response to the bed body being located at the working position, the electrically conductive body and the electrically conductive rail are configured to engage in electrical energy transmission through contact.

6. The movable medical bed system as claimed in claim 1, wherein:
the bed body is movable to the working position in a docking direction that corresponds to the second direction;
the movable medical bed system further comprises a docking guidance apparatus, which includes an insertion member and a guiding member, one of the insertion member and the guiding member being fixed to the bed body;
the guiding member has a plug-in slot;
the insertion member is configured to be inserted into the plug-in slot of the guiding member as the bed body moves to the working position in the docking direction; and
in response to the bed body being located at the working position, a slot wall of the plug-in slot is configured, through abutment with the insertion member, to restrict shifting of the bed body in a direction perpendicular to the docking direction.

7. The movable medical bed system as claimed in claim 6, wherein:
a free end of the insertion member has a pointed shape, gradually contracting toward a center in the docking direction; and
a bottom of the plug-in slot, in the docking direction, has a same shape as the free end of the insertion member.

8. The movable medical bed system as claimed in claim 1, wherein the movable medical bed system further comprises:
a wireless communication receiver arranged on the bed body, the wireless communication receiver being configured to receive a drive control signal by wireless telecommunication or optical wireless communication;
a drive controller arranged on the bed body and connected to the wireless communication receiver to receive the drive control signal, the drive controller being configured to acquire electrical energy via the electrical energy receiver; and
an electric motor arranged on the bed body and connected to the drive controller, the drive controller being configured to control the electric motor based on the drive control signal.

9. The movable medical bed system as claimed in claim 8, wherein the movable medical bed system further comprises a battery, the drive controller being connected to the battery to acquire electrical energy, and the electrical energy receiver being connected to the battery to charge the battery.

10. The movable medical bed system as claimed in claim 8, wherein the movable medical bed system further comprises:
an operating panel configured to generate the drive control signal based on an operation performed thereon by a user; and
a wireless communication transmitter connected to the operating panel, the operating panel being configured to send the drive control signal to the wireless communication receiver via the wireless communication transmitter by wireless telecommunication or optical wireless communication.

11. The movable medical bed system as claimed in claim 8, wherein the bed body further comprises:
at least two rollers configured to support the bed frame above the ground surface in the first direction, the bed frame being movable using the at least two rollers; and a bed board movably connected to the bed frame, the electric motor being configured to drive the bed board to move relative to the bed frame.

12. The movable medical bed system as claimed in claim 1, wherein the movable medical bed system further comprises a communication device, the communication device being arranged on the bed body and comprising:
an analog-to-digital converter configured to connect to radio-frequency (RF) coil;
a digital signal processor connected to the analog-to-digital converter, and
a wireless communication transmitter and/or receiver connected to the digital signal processor and configured to communicate with a control system by wireless telecommunication or optical wireless communication.

13. A magnetic resonance imaging (MRI) apparatus, comprising a movable medical bed system as claimed in claim 1.

14. A magnetic resonance imaging (MRI) apparatus, comprising:
a movable medical bed system according to claim 1, wherein the movable medical bed system further includes:
a wireless communication receiver arranged on the bed body, the wireless communication receiver being configured to receive a drive control signal by wireless telecommunication or optical wireless communication;
a drive controller arranged on the bed body and connected to the wireless communication receiver to receive the drive control signal, the drive controller being configured to acquire electrical energy via the electrical energy receiver; and
an electric motor arranged on the bed body and connected to the drive controller, the drive controller being configured to control the electric motor based on the drive control signal;
a control system configured to generate a drive control signal; and
a wireless communication transmitter connected to the control system, the control system being configured to send the drive control signal to the wireless communication receiver via the wireless communication transmitter by wireless telecommunication or optical wireless communication.

15. A magnetic resonance imaging (MRI) apparatus, comprising:
a movable medical bed system according to claim 1, wherein the movable medical bed system further comprises a communication device arranged on the bed body, the communication device including:
an analog-to-digital converter configured to connect to a radio-frequency (RF) coil;
a digital signal processor connected to the analog-to-digital converter, and
a wireless communication transmitter and/or receiver connected to the digital signal processor and configured to communicate with a control system by wireless telecommunication or optical wireless communication;
the RF coil connected to the analog-to-digital converter;
a control system; and
a wireless communication transmitter connected to the control system and configured to communicate with the wireless communication transmitter and/or receiver of the communication device by wireless telecommunication or optical wireless communication.

16. The movable medical bed system as claimed in claim 1, wherein:
the first shielding cover comprises a first opening and the second shielding cover comprises a second opening; and
in response to the bed body being located at the working position, the first opening of the first shielding cover and the second opening of the second shielding cover are positioned opposite each other in the first direction and configured to engage each other in the first direction to form the shielding space.

17. The movable medical bed system as claimed in claim 1, wherein:
the bed body further comprises rollers configured to support the bed frame above the ground surface in the first direction, the bed frame being movable using the at least two rollers; and
the electrical energy receiver is disposed in a portion of the bottom of the bed frame located between the rollers in the second direction and a third direction perpendicular to the first and the second directions.

18. The movable medical bed system as claimed in claim 1, wherein the electrical energy transmitter is disposed below the ground surface.

19. The movable medical bed system as claimed in claim 1, wherein
the electrical energy receiver is spaced above the ground surface in the first direction and spaced from the electrical energy transmitter in the first direction.

20. A magnetic resonance imaging (MRI) apparatus, comprising:
a movable medical bed system including:
a bed body including a bed frame, a bottom of the bed frame being spaced above a ground surface in a first direction;
a power supply apparatus, including: an electrical energy receiver disposed at the bottom of the bed frame;
an electrical energy transmitter disposed on or below the ground surface and configured to be connected to a power source, the bed body being moveable to a working position relative to the electrical energy transmitter in a second direction perpendicular to the first direction, wherein, in response to the bed body being located at the working position, the electrical energy receiver being spaced from the electrical energy transmitter in the first direction and configured to engage in electrical energy transmission, in the first direction, with the electrical energy transmitter without plugging-in;
a first shielding cover arranged on the bed frame and being configured to shield an electromagnetic field; a second shielding cover configured to shield an electromagnetic field,
wherein, in response to the bed body being located at the working position, the first shielding cover and the second shielding cover are arranged opposite one another in the first direction, and the first shielding cover is configured to move away from the bottom of the bed frame towards the second shielding cover to reduce a distance between the first shielding cover and the second shield cover in the first direction and collectively define a shielding space, the electrical energy receiver and the electrical energy transmitter being located in the shielding space;
a wireless communication receiver arranged on the bed body, the wireless communication receiver being configured to receive a drive control signal by wireless telecommunication or optical wireless communication;

a drive controller arranged on the bed body and connected to the wireless communication receiver to receive the drive control signal, the drive controller being configured to acquire electrical energy via the electrical energy receiver; and an electric motor arranged on the bed body and connected to the drive controller, the drive controller being configured to control the electric motor based on the drive control signal;

a control system configured to generate a drive control signal; and a wireless communication transmitter connected to the control system, the control system being configured to send the drive control signal to the wireless communication receiver via the wireless communication transmitter by wireless telecommunication or optical wireless communication.

21. A magnetic resonance imaging (MRI) apparatus, comprising:

a movable medical bed system including: a bed body including a bed frame, a bottom of the bed frame being spaced above a ground surface in a first direction;

a power supply apparatus, including:

an electrical energy receiver disposed at the bottom of the bed frame; an electrical energy transmitter disposed on or below the ground surface and configured to be connected to a power source, the bed body being moveable to a working position relative to the electrical energy transmitter in a second direction perpendicular to the first direction, wherein, in response to the bed body being located at the working position, the electrical energy receiver being spaced from the electrical energy transmitter in the first direction and configured to engage in electrical energy transmission, in the first direction, with the electrical energy transmitter without plugging-in;

a first shielding cover arranged on the bed frame and being configured to shield an electromagnetic field;

a second shielding cover configured to shield an electromagnetic field, wherein, in response to the bed body being located at the working position, the first shielding cover and the second shielding cover are arranged opposite one another in the first direction, and the first shielding cover is configured to move away from the bottom of the bed frame towards the second shielding cover to reduce a distance between the first shielding cover and the second shield cover in the first direction and collectively define a shielding space, the electrical energy receiver and the electrical energy transmitter being located in the shielding space; and a communication device, the communication device being arranged on the bed body and including:

an analog-to-digital converter configured to connect to a radio-frequency (RF) coil;

a digital signal processor connected to the analog-to-digital converter, and a wireless communication transmitter and/or receiver connected to the digital signal processor and configured to communicate with a control system by wireless telecommunication or optical wireless communication;

the RF coil connected to the analog-to-digital converter;

a control system; and a wireless communication transmitter connected to the control system and configured to communicate with the wireless communication transmitter and/or receiver of the communication device by wireless telecommunication or optical wireless communication.

* * * * *